United States Patent [19]

Fong

[11] Patent Number: 5,043,406

[45] Date of Patent: Aug. 27, 1991

[54] FLUORESCENT ACRYLAMIDE POLYMERS

[75] Inventor: Dodd W. Fong, Naperville, Ill.

[73] Assignee: Nalco Chemical Company, Naperville, Ill.

[21] Appl. No.: 581,937

[22] Filed: Sep. 13, 1990

Related U.S. Application Data

[63] Continuation-in-part of Ser. No. 498,657, Mar. 26, 1990, abandoned.

[51] Int. Cl.$^5$ .................. C08F 222/38; C08F 2/00; C08F 220/04
[52] U.S. Cl. .................. 526/304; 526/207; 526/328
[58] Field of Search .................. 526/304, 207

[56] References Cited

U.S. PATENT DOCUMENTS 4,813,973 3/1989 Winnik et al.

OTHER PUBLICATIONS

Borg, Robert; Winnik, Mitchell A.; Attachment of Fluorescent Dyes to Polyacrylamides in Aqueous Media, Journal of Polymer Science, Part A: Polymer Chemistry 28(8), 2075–2083, 1990.

Chemical Abstract 113:98189t, 1990.

Hans G. Boit, Beilsteins Handbuch der Organischen Chemie, 4th Edition, vol. 18, Part 8, pp. 7217–7218 (1976).

H. W. Bond and G. W. Luttermoser, Studies on the Chemotherapy of Experimental Schistosomiasis, Journal of the American Pharmaceutical Assn., 43, 22 (1954).

Primary Examiner—Joseph L. Schofer
Assistant Examiner—Wu C. Cheng
Attorney, Agent, or Firm—John G. Premo; Robert A. Miller

[57] ABSTRACT

Water soluble polymers containing N-9-xanthenylacrylamide and N-dibenzosuberenylacrylamide.

3 Claims, No Drawings

FLUORESCENT ACRYLAMIDE POLYMERS

INTRODUCTION

This application is a continuation in part of my co-pending application Ser. No. 07/498,657 filed Mar. 26, 1990, now abandoned for Fluorescent Acrylamide Monomer and Polymers.

It has been known that acrylamide polymers can be modified in aqueous solution with organic die molecules which can form stable carbo-cations reversibly in water (U.S. Pat. No. 4,813,973). An example of a suitable dye is dibenzosuberenol. Polymers were tagged by mixing the dye with polyacrylamide in a dilute aqueous solution with an acid catalyst at room temperature for 10 to 24 hours. The polymers were recovered by precipitation in methanol and analyzed spectrophotometrically. The process requires the dissolution of the polymer to be tagged in water and the polymer has to be acrylamide based.

The modification of polyacrylamide in dilute aqueous or mixed solvent system is not very practical. Copolymerization with a fluorescent monomer would be a better alternative to prepare tagged polymers especially for systems like high molecular weight cationic polymers.

GENERAL STATEMENT OF THE INVENTION

I have found new acrylamide monomers with fluorescent groups such as N-dibenzosuberenylacrylamide (N-5-(5H-dibenzo[a,d]cycloheptenyl)acrylamide, readily can be prepared. Fluorescent acrylamide and non-acrylamide base polymers can readily be prepared by copolymerization with the fluorescent acrylamide monomers. This process is more economical and practical for commercial use than the process described in U.S. Pat. No. 4,813,973.

THE INVENTION

The invention comprises the N-substituted acrylamide polynuclear aromatic fluorescent dye from the group consisting of:
A. N-9-xanthenylacrylamide, and
B. N-dibenzosuberenylacrylamide (N-5-)5H-dibenzo[a,d]cycloheptenyl)acrylamide).

The invention also comprises a water soluble vinyl polymer which contains at least one water soluble vinyl monomer and from 0.01–2.0 mole% of either of the two vinyl monomers, N-9-xanthenylacrylamide and N-dibenzosuberenylacrylamide. These water soluble vinyl polymers are prepared by vinyl addition polymerization. In a preferred embodiment, the water soluble vinyl polymers that are modified using the vinyl monomers N-9-xanthenylacrylamide and N-dibenzosuberenylacrylamide are most preferably those water soluble polymers prepared from the monomers acrylamide, acrylic acid and mixtures thereof.

Water soluble cationic monomers can be modified in accordance with the teachings of the invention are illustrated by such monomers as diallyldimethyl ammonium chloride and dimethylaminoethyl acrylate and diethyldimethylaminopropylmethacrylate.

The amount of either monomer N-9-xanthenylacrylamide or N-dibenzosuberenylacrylamide that may be co-polymerized with the monomers described above will vary from as little as 0.01–2 mole%. Since the novel acrylamide monomers of the invention are water insoluble the amount used in preparing water soluble polymers should not be such as to reduce the solubility of the product sought to be tagged.

PREPARATION OF THE ACRYLAMIDE MONOMERS

The reaction media may be water, acetic acid, formic acid, or in water-acetic acid or water-formic acid mixtures. Preferred solvents contain from 5% to 90% acetic or formic acids. The reaction temperature is from 0° C. to 40° C., preferably 10° C. to 30° C.

In all of the examples below, the acrylamide used was an aqueous 40% solution.

EXAMPLE 1

Preparation of N-9-xanthenylacrylamide

| REAGENTS: | |
|---|---|
| Glacial acetic acid | 25 g |
| Acrylamide Formula weight = 71 | 5 g (0.0704 mol) |
| 9-hydroxyxanthene | 1 g (0.0049 mol) |

REACTION CONDITIONS

The acrylamide was dissolved in the acetic acid, then the 9-hydroxyxanthene was added while stirring. The mixture was covered with foil and stirred for 48 hours. The product separated as a precipitate. The precipitate was filtered, washed with water and subsequently dried.

The C13 NMR spectrum of this sample is consistent with the anticipated N-9-xanthenylacrylamide.

EXAMPLE 2

Preparation of N-dibenzosuberenylacrylamide

| REAGENTS: | |
|---|---|
| Acetic Acid | 50 g |
| Acrylamide | 10 g (0.141 mole) |
| Dibenzosuberenol | 2.04 g (0.010 mole) |

REACTION CONDITIONS

Dibenzosuberenol was added with stirring into an acetic acid solution of acrylamide at room temperature.

RESULTS

A clear yellow solution was formed. After stirring at room temperature for 24 hours, a white solid separated from solution. The solid isolated was washed with water and methanol.

The IR and C13 NMR spectra of this sample is consistent with the anticipated N-dibenzosuberenylacrylamide.

EXAMPLE 3

Batch polymerization of acrylic acid and N-dibenzosuberenylacrylamide.

| | REAGENTS: | |
|---|---|---|
| | Acrylic Acid | 50.75 g |
| A | 27.2% solution of N-dibenzosuberenyl-acrylamide in trifluoroacetic acid | 3.73 g (2 wt % (0.6 mole %) of monomer) |
| | H₂O, DI | 54.97 g |
| | Ammonium persulfate | 0.89 g |

| | REAGENTS: | |
|---|---|---|
| B | H₂O, DI | 16 g |
| C | Sodium bisulfite | 2.66 g |
| | H₂O, DI | 16 g |

Monomer solution A was charged into a 300-ml Parr reactor. The solution was heated to 35° C. and initiator solutions B and C were added into the monomer solution with stirring. The valves of the reactor were quickly closed. The reaction mixture was warmed up slowly and an exothermic reaction occurred at about 50° C. and the temperature rose quickly to 135° C. After the reaction was completed, the polymer was characterized by GPC using UV and fluorescence detectors. Results show the polymer was fluorescent.

EXAMPLE 4

Batch polymerization of acrylic acid, acrylamide and N-dibenzosuberenylacrylamide.

| | REAGENTS: | |
|---|---|---|
| A | Acrylic Acid | 25.55 g |
| | Acrylamide (48.4% solution) | 52.07 g |
| | 50% NaOH | 12.64 g |
| | 27.2% Soln of N-dibenzosuberenyl-acrylamide in trifluoroacetic acid | 3.23 g (1.7 wt % (0.5 mole %) of monomers) |
| | pH of the monomer solution = 5.0 | |
| B | H₂O, DI | 19.19 g |
| | Ammonium Persulfate | 0.89 g |
| | H₂O, DI | 16.0 g |
| C | Sodium Bisulfite | 2.66 g |

| REAGENTS: | |
|---|---|
| H₂O, DI | 16 g |

Monomer solution A was charged into a 300-ml Parr reactor. The solution was heated to 35° C. and initiator solutions B and C were added into the monomer solution with stirring. The valves of the reactor were quickly closed. The reaction was highly exothermic and the temperature of reaction mixture rose quickly to about 140° C. After the reaction was completed, the polymer was characterized by GPC using UV and fluorescence detectors. Results show the polymer was fluorescent.

CONCLUSION

N-9-xanthenylacrylamide and N-dibenzosuberenylacrylamide monomers have been prepared and characterized by NMR and IR. The 9-xanthenylacrylamide group shows little fluorescence. However, the N-dibenzosuberenylacrylamide group shows strong fluorescence at 345 nm (ex 295 nm). Polyacrylic acid and poly(acrylic acid-acrylamide) prepared with 2 wt. % of N-dibenzosuberenylacrylamide comonomer show fluorescence at 345 nm and can be detected readily with a fluorometer.

Having thus described my invention it is claimed as follows:

I claim:

1. A water soluble polymer from the group consisting of acrylic acid, acrylamide and mixtures thereof, which contains from 0.1–2.0 mole % of N-dibenzosuberenylacrylamide (N-5-(5H-dibenzo {a,d} cycloheptenyl)acrylamide) said water soluble vinyl polymer having been prepared by vinyl addition polymerization.

2. The water soluble vinyl polymer of claim 1 where the water soluble vinyl monomer is acrylic acid.

3. The water soluble vinyl polymer of claim 1 where the water soluble vinyl monomer is acrylamide.

* * * * *